US010561774B2

(12) United States Patent
Voskoboynikov et al.

(10) Patent No.: US 10,561,774 B2
(45) Date of Patent: *Feb. 18, 2020

(54) HVAD CIRCADIAN TRACKER (PHI+)

(71) Applicant: HeartWare, Inc., Miami Lakes, FL (US)

(72) Inventors: Neil Voskoboynikov, Pembroke Pines, FL (US); Pedro E. Grave De Peralta, Hialeah, FL (US); Veronica Ramos, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 119 days.

This patent is subject to a terminal disclaimer.

(21) Appl. No.: 15/648,735

(22) Filed: Jul. 13, 2017

(65) Prior Publication Data
US 2019/0015571 A1 Jan. 17, 2019

(51) Int. Cl.
A61M 1/12 (2006.01)
A61M 1/10 (2006.01)

(52) U.S. Cl.
CPC ............ A61M 1/122 (2014.02); A61M 1/101 (2013.01); A61M 1/1086 (2013.01); A61M 2205/3327 (2013.01)

(58) Field of Classification Search
None
See application file for complete search history.

(56) References Cited

U.S. PATENT DOCUMENTS

| 7,997,854 | B2 | 8/2011 | LaRose et al. |
| 8,419,609 | B2 | 4/2013 | Shambaugh, Jr. et al. |
| 2008/0242943 | A1 | 10/2008 | Cuddihy et al. |
| 2017/0119256 | A1 | 5/2017 | Demou et al. |
| 2017/0136164 | A1* | 5/2017 | Yeatts ................... G08B 21/18 |
| 2017/0215261 | A1* | 7/2017 | Potucek ............... A61H 33/005 |
| 2018/0024578 | A1* | 1/2018 | Ahuja ..................... G06F 1/206 |
| | | | 700/300 |

FOREIGN PATENT DOCUMENTS

WO 2005030296 A2 4/2005
WO 2015183922 A1 12/2015

OTHER PUBLICATIONS http://www.investopedia.com/terms/m/macd.asp.
Seppo Voutilainen et al., Circadian variation of left ventricular diastolic function in healthy people, Heart, 1996; 74:35-39.
(Continued)

Primary Examiner — Erica S Lee
(74) Attorney, Agent, or Firm — Christopher & Weisberg, P.A.

(57) ABSTRACT

A method of detecting a disruption in a diurnal rhythm of a patient having an implantable blood pump comprising calculating a moving average convergence divergence (MACD) based on power consumed by the implantable blood pump to maintain a constant rotational speed of an impeller of the implantable blood pump and generating an alert when the calculated MACD does not cross a MACD zero line for a predetermined MACD zero line crossing time threshold.

20 Claims, 10 Drawing Sheets

(56) References Cited

OTHER PUBLICATIONS

Pietro Cugini et al., Circadian Rhythm of Cardiac Output, Peripheral Vascular Resistance, and Related Variables by a Beat-to-Beat Monitoring, Chronobiology International, vol. 10, No. 1, pp. 73-78.
Yukihito Higashi, MD, PHD et al., Circadian Variation of Blood Pressure and Endothelial Function in Patients With Essential Hypertension: A Comparison of Dippers and Non-Dippers, Journal of the American College of Cardiology, vol. 40, No. 11, 2002.
Levent Undar et al., Circadian Variation in Circulating Platelet Aggregates, Annals of Medicine 21: 429-433, 1989.
International Search Report and Written Opinion dated Mar. 27, 2018, for corresponding International Application No. PCT/US2017/041859; International Filing Date: Jul. 13, 2017 consisting of 11-pages.

* cited by examiner

HVAD CIRCADIAN TRACKER (PHI+)

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a method and system for detecting a disruption in a diurnal rhythm of a patient having an implantable blood pump.

BACKGROUND

Ventricular assist devices, or VADs, are lifesaving mechanical circulatory support devices, or MCSDs, configured to assist the heart in pumping blood throughout the body. VADs may include centrifugal pumps, axial pumps, or other kinds electromagnetic pumps configured to pump blood from the heart to blood vessels to circulate around the body. One such centrifugal pump is the HVAD sold by HeartWare, Inc. and is shown and described in U.S. Pat. No. 7,997,854 the entirety of which is incorporated by reference. One such axial pump is the MVAD sold by HeartWare, Inc. and is shown and described in U.S. Pat. No. 8,419,609 the entirety of which is incorporated herein by reference.

Detecting patient adverse events associated with the implantation of VADs is challenging owing to the fact that patients requiring such devices often have different cardiac pathology that necessitated the implantation of the VAD within the patient. One solution devised is to implant sensors into or onto the VAD to detect operating parameters of the blood pump. Implanting sensors within or onto VADS, however, requires sensor calibration, are subject to potential failure from corrosion or other events, and increases the power necessary to operate the VAD.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method of detecting a disruption in a diurnal rhythm of a patient having an implantable blood pump, including: calculating a moving average convergence divergence (MACD) based on power consumed by the implantable blood pump to maintain a constant rotational speed of an impeller of the implantable blood pump; and generating an alert when the calculated MACD does not cross a MACD zero line for a predetermined MACD zero line crossing time threshold. Other embodiments of this aspect include corresponding computer systems, apparatus, and computer programs recorded on one or more computer storage devices, each configured to perform the actions of the methods.

Implementations may include one or more of the following features. The method where the MACD zero line crossing time threshold is 24 hours. The method where calculating the MACD includes calculating a slow moving average (SMA), and where the SMA is a one second average measurement of the power consumed by the implantable blood measured at a predetermined interval for a first predetermined period of time. The method where the predetermined interval is 15 minutes. The method where the first predetermined period of time is 48 hours. The method where calculating the MACD includes calculating a fast moving average (FMA), and where the FMA is a one second average measurement of the power consumed by the implantable blood measured at the predetermined interval for a second predetermined period of time less the first period of time. The method where the second predetermined period of time is four hours. The method where the patient has a diurnal cycle, and where generating the alert is indicative of a loss of the patient's diurnal cycle. The method where the method further includes correlating the loss of the patient's diurnal cycle to at least one from the group including of thrombus and tachycardia. The method generating an alert includes at least one from group including of sounding an alarm on a controller of the implantable blood pump and displaying a time and date of the alert in a log file of a controller of the implantable blood pump. Implementations of the described techniques may include hardware, a method or process, or computer software on a computer-accessible medium.

One general aspect includes a system of detecting a disruption in a diurnal rhythm of a patient having an implantable blood pump, including: a controller having a processor, the controller being in communication with the implantable blood pump and a power source configured to provide power to the implantable blood pump, the controller being configured to calculate a moving average convergence divergence (MACD) based on power consumed by the implantable blood pump to maintain a constant rotational speed of an impeller of the implantable blood pump; and generate an alert when the calculated MACD does not cross a MACD zero line for a predetermined MACD zero line crossing time threshold. Other embodiments of this aspect include corresponding computer systems, apparatus, and computer programs recorded on one or more computer storage devices, each configured to perform the actions of the methods.

Implementations may include one or more of the following features. The system where the MACD zero line crossing time threshold is 24 hours. The system where calculating the MACD includes calculating a slow moving average (SMA), and where the SMA is a one second average measurement of the power consumed by the implantable blood measured at a predetermined interval for a first predetermined period of time. The system where the predetermined interval is 15 minutes. The system where the first predetermined period of time is 48 hours. The system where calculating the MACD includes calculating a fast moving average (FMA), and where the FMA is a one second average measurement of the power consumed by the implantable blood measured at the predetermined interval for a second predetermined period of time less the first period of time. The system where the second predetermined period of time is four hours. The system generating an alert includes at least one from group including of sounding an alarm on a controller of the implantable blood pump and displaying a time and date of the alert on a display of a controller of the implantable blood pump. The system where the controller is further configured to clear the alert when the calculated MACD crosses the MACD zero line for the predetermined MACD zero line crossing time threshold. Implementations of the described techniques may include hardware, a method or process, or computer software on a computer-accessible medium.

One general aspect includes a method of detecting a disruption in a diurnal rhythm of a patient having an implantable blood pump and a diurnal cycle, including: calculating a moving average convergence divergence (MACD) based on power consumed by the implantable blood pump to maintain a constant rotational speed of an impeller of the implantable blood pump. The method also includes generating an alert when the calculated MACD does not cross a MACD zero line for a predetermined MACD zero line crossing time threshold, the alert being indicative of a loss of the patient's diurnal cycle, the generating an alert includes at least one from group including of sounding an alarm on a controller of the implantable blood pump and displaying a time and date of the alert in a log file of a controller of the implantable blood pump. The method also includes correlating the loss of the patient's diurnal cycle to at least one from the group including of thrombus and tachycardia. The method also includes clearing the alert when the calculated MACD crosses the MACD zero line for the predetermined MACD zero line crossing time threshold. Other embodiments of this aspect include corresponding computer systems, apparatus, and computer programs recorded on one or more computer storage devices, each configured to perform the actions of the methods.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
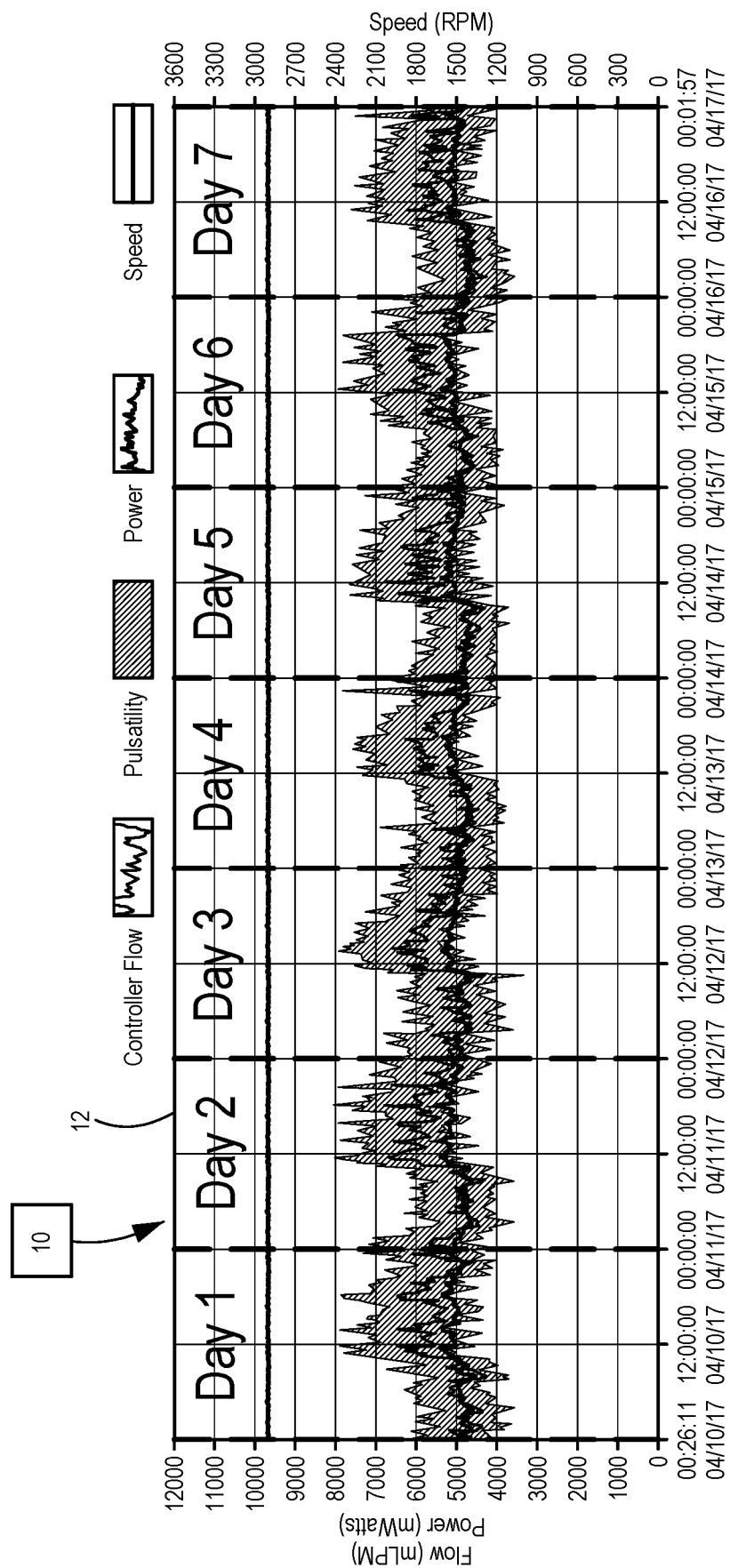
FIG. 1 is an exemplary display of a log file of an implantable blood pump operating within normal parameters.

Referring now to the drawings in which like reference designators refer to like elements, there is shown in FIG. 1 a controller 10 and an exemplary log file 12 constructed in accordance with the principles of the present application. The controller 10 may include a processor having processing circuity configured to measure parameters of a blood pump implanted within a human or animal patient and to control the operation of the implantable blood pump. As used herein, an implantable blood pump refers to any MCSD, such as HVAD, and MVAD, having movable element, such as impeller, configured to pump blood from the heart to the patient's circulatory system. The controller 10 be may in communication with the implantable blood pump through one or more conductors (not shown) and measures parameters such as flow rate out of the pump in mL/pin, power consumption in mWatts, and the rotational speed of the impeller in RPM. The controller 10 is configured to measure a one second average these parameters at a predetermined interval and record these parameters in controller log files 12 stored in the controller 10. For example, in the log file 12 shown in FIG. 1, the controller 10 averages flow rate, power, and speed of the impeller by average the measurement of each parameter over a one second interval every 15 minutes and records the same on the log file 12 which can be displayed in graphical form on a computer as shown in the exemplary log file 12 in FIG. 1. The 15 minute interval may be variable as well as the one second average. For example, it is fully contemplated that any interval, for example, 1-60 minutes may be used to sample the measured parameters from the blood pump and the average may be over, for example, 1-5 seconds. Measuring the one second average of the measured parameters every 15 min helps to reduce noise in the log file 12.

Figure 2:
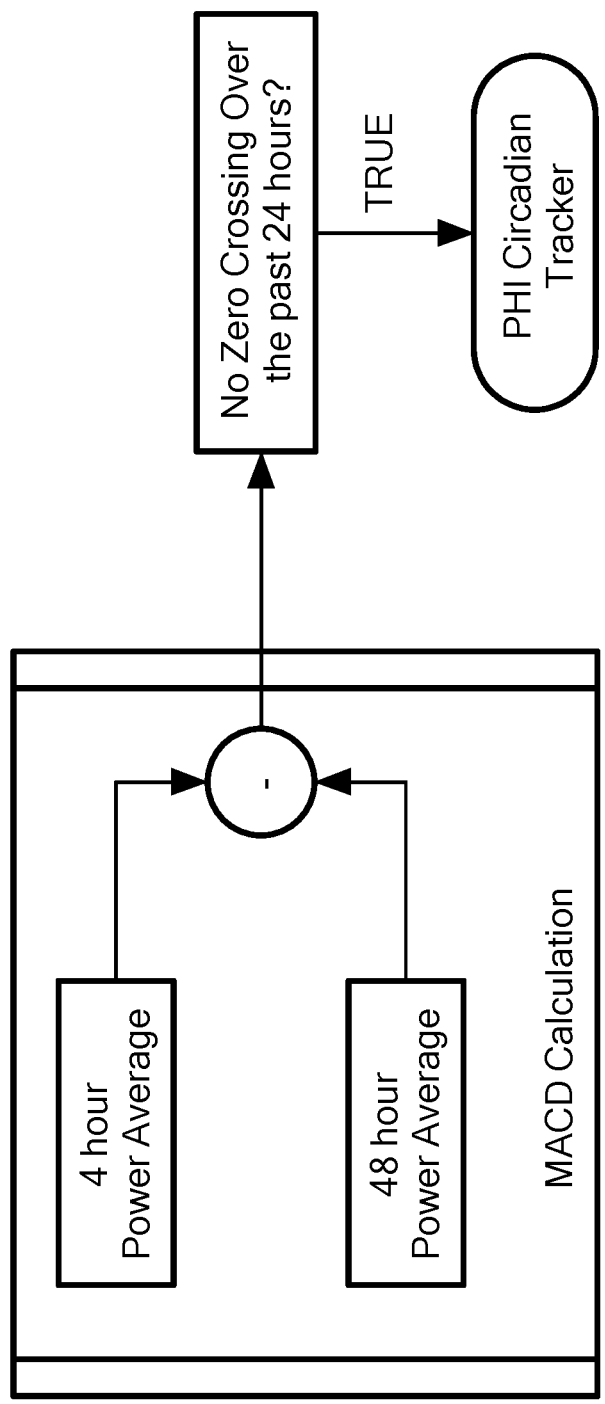
FIG. 2 is an exemplary flow chart showing a method of determining a disruption in circadian rhythm in a patient with an operating blood pump in accordance with the present application.

Referring now to FIG. 2, the controller 10 is further configured to calculate a moving average convergence divergence (MACD) based on power consumed by the implantable blood pump to maintain a constant rotational speed of an impeller of the implantable blood pump. As used here, the MACD refers a trend-following indicator that shows the relationship between two moving averages of the same parameter. In the exemplary embodiment shown in FIG. 2, calculating the MACD includes calculating a slow moving average (SMA) and a fast moving average (FMA). The SMA is a one second average measurement of the power consumed by the implantable blood measured at a predetermined interval for a first predetermined period of time. In an exemplary configuration, the predetermined interval for the SMA is 15 minutes and the first predetermined period of time of 48 hours. In other configurations, the first predetermined period of time maybe be longer or shorter than 48 hours. The FMA is a one second average measurement of the power consumed by the implantable blood measured at the predetermined interval for a second predetermined period of time less the first period of time. For example, the FMA may be calculated over the predetermined interval of 15 minutes and for second period of time of four hours. The MACD is calculated by subtracting the SMA from FMA to create an index showing trends in power consumed by the implantable blood pump.

Continuing to refer to FIG. 2, when the calculated MACD does not cross a MACD zero line for a predetermined MACD zero line crossing time threshold an alert is generated. For example, while the calculated MACD may vary in amplitude, mean level, and rhythmic and non-rhythmic components, if the MACD level does not cross the zero line during a crossing time threshold, for example, 24 hours, it is indicative of a loss in a patient's diurnal rhythm. Because the MACD compares to moving averages, namely, the SMA and FMA, the reference is based on a zero, i.e. either the FMA is above the MACD will be above zero when the FMA is greater than the SMA and below zero when the FMA is less than the SMA. However, in a patient having a normal diurnal cycle, the MACD should cross the zero line at least once every 24 hours. When the calculated MACD does not cross a MACD zero line for the predetermined MACD zero line crossing time threshold an alert is generated and the patient's diurnal cycle has been interrupted or lost. The alert may include sounding an alarm on the controller 10 of the implantable blood pump and/or displaying a time and date of the alert in a log file 12 of the controller 10. The alert may further include flagging in the log file the 24 hour period or more than one 24 hour period in which the MACD calculation does not cross the zero line. For example, the log file 12 when displayed on a computer, may mark the 24 hours periods in which no zero crossings have occurred in a different color than the background display for easy recognition. The controller 10 and/or the physician reviewing the log files 12 may correlate the loss of the patient's diurnal cycle to adverse events such as thrombus, tachycardia, arrhythmia, and GI bleeding. The alert may be cleared the alert when the calculated MACD crosses the MACD zero line for the predetermined MACD zero line crossing time threshold. For example. If the MACD crosses the zero line, the shaded area or otherwise flagged area of log file is removed indicating normal operation for that time period.

Figure 3:
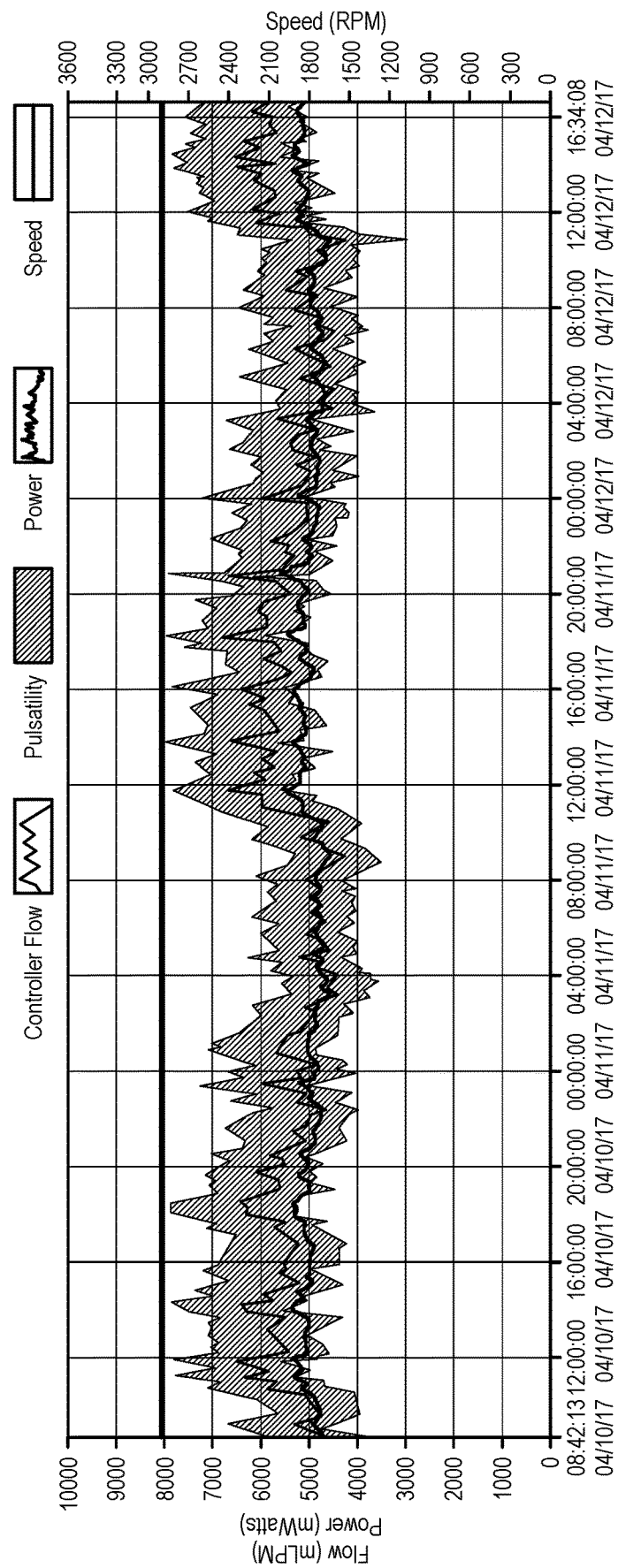
FIG. 3 is an exemplary display of a log file of an implantable blood pump operating within normal parameters.
Figure 4:
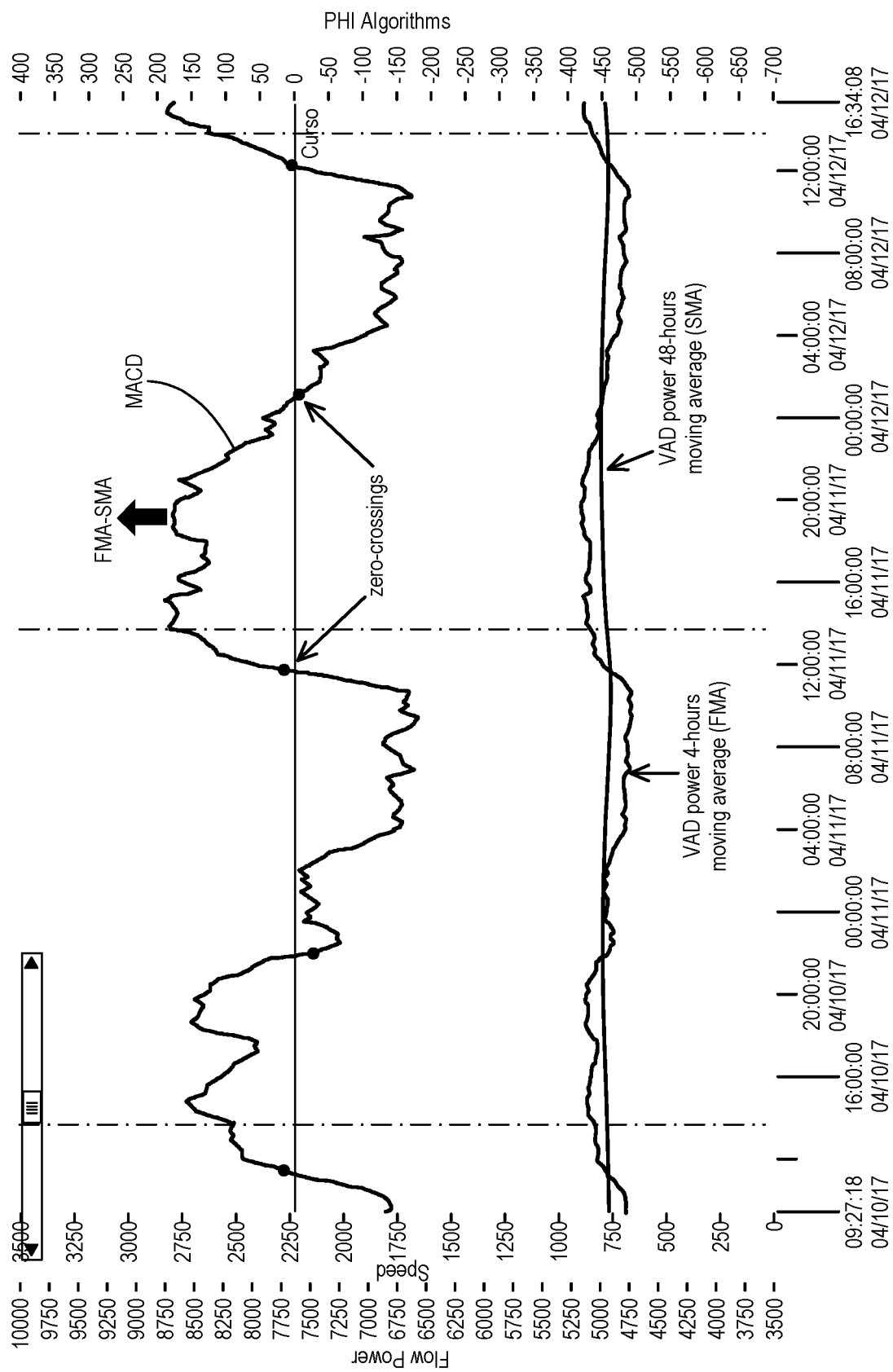
FIG. 4 is the log file of FIG. 3 with an MACD calculation displayed over a two-day period and operating within normal parameters.

Referring now to FIGS. 3 and 4, in this exemplary log file 12 of a patient whose pump is operating in homeostasis, the MACD is displayed above the SMA and FMA trends line (FIG. 4) and shows a smooth trend line where power increases during that day and decreases at night. The MACD further crosses the zero line at least once every 24 hours. Such crossings are indicated by a bullet point or other indicia such that they are readily visible on the log file. For example, as shown in FIG. 4, between Apr. 10, 2017 and Apr. 12, 2017, the MACD crosses the zero-line five times. Thus, in this exemplary log file 12 no alert was generated and there is no indication of adverse events.

Figure 5:
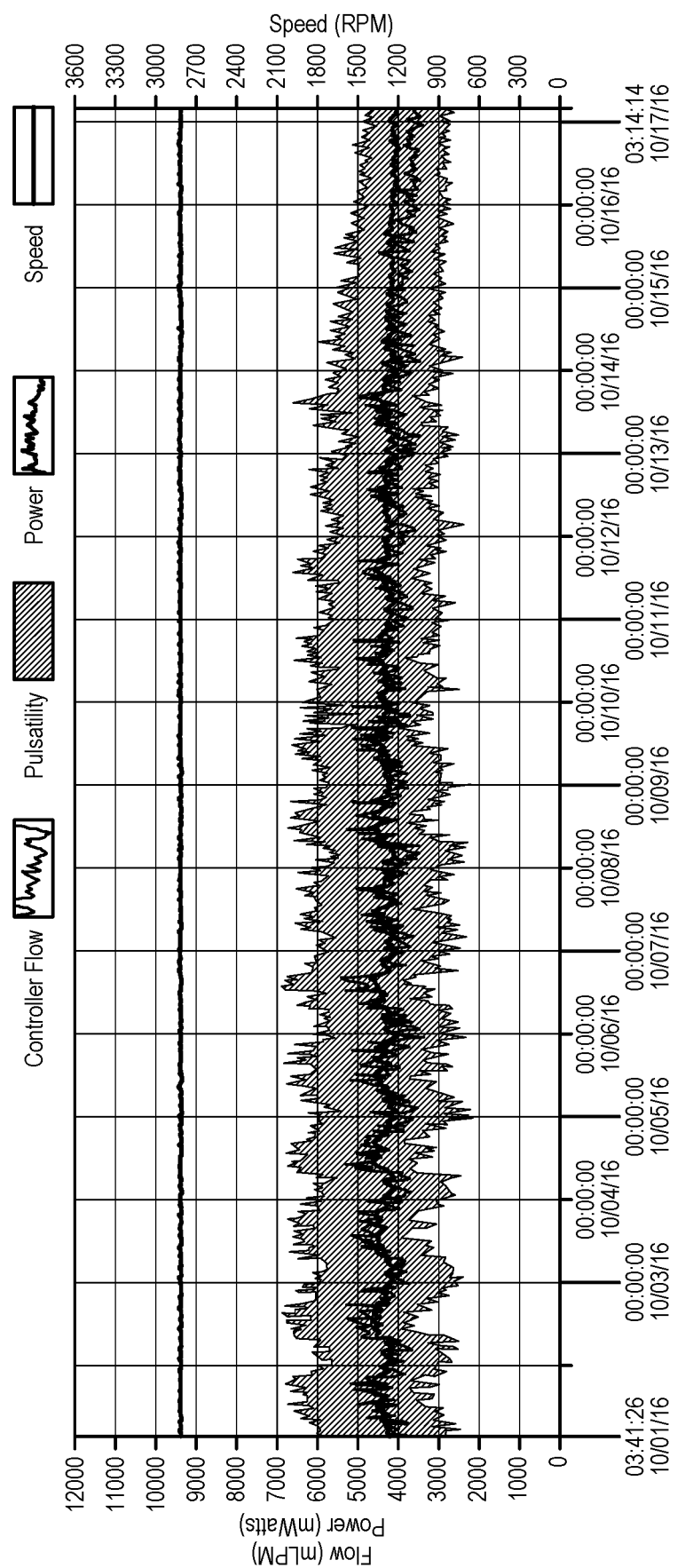
FIG. 5 is an exemplary display of a log file of an implantable blood pump operating abnormally.
Figure 6:
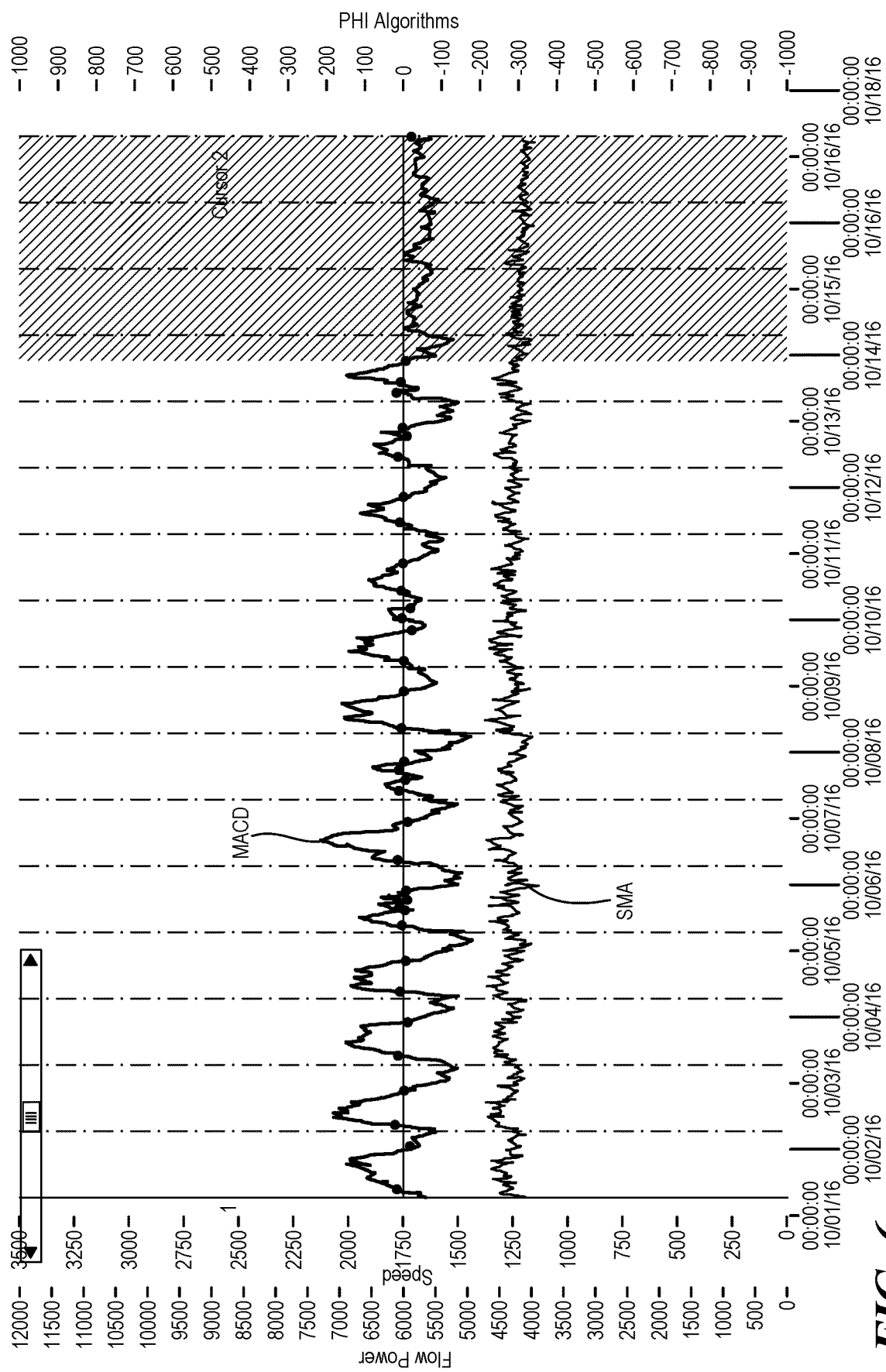
FIG. 6. is the log file of FIG. 5 with an MACD calculation displayed indicating a loss of circadian rhythm.

Referring now to FIGS. 5 and 6, in this exemplary log file 12 of a patient whose pump is operating is not operating homeostasis, the MACD is displayed above the SMA trend line (FIG. 6). Between Oct. 1, 2016 and Oct. 14, 2016, the MACD crosses the zero-line at least once every 24 hours as indicated by the bullets on the MACD trend line at zero-crossings. However, beginning about Oct. 14, 2016, at least one 24 hour period of no zero-crossings begin in which the MACD trend line stays below zero. The controller 10 shades the area in which no zero-crossings occur for at least 24 hours such that the physician can determine when the disruption in homeostasis of the blood pump occurred and for how long it lasted. In this particular example, the lack of zero-crossings for four consecutive days is indicative in the loss of the patient's circadian rhythm.

Figure 7:
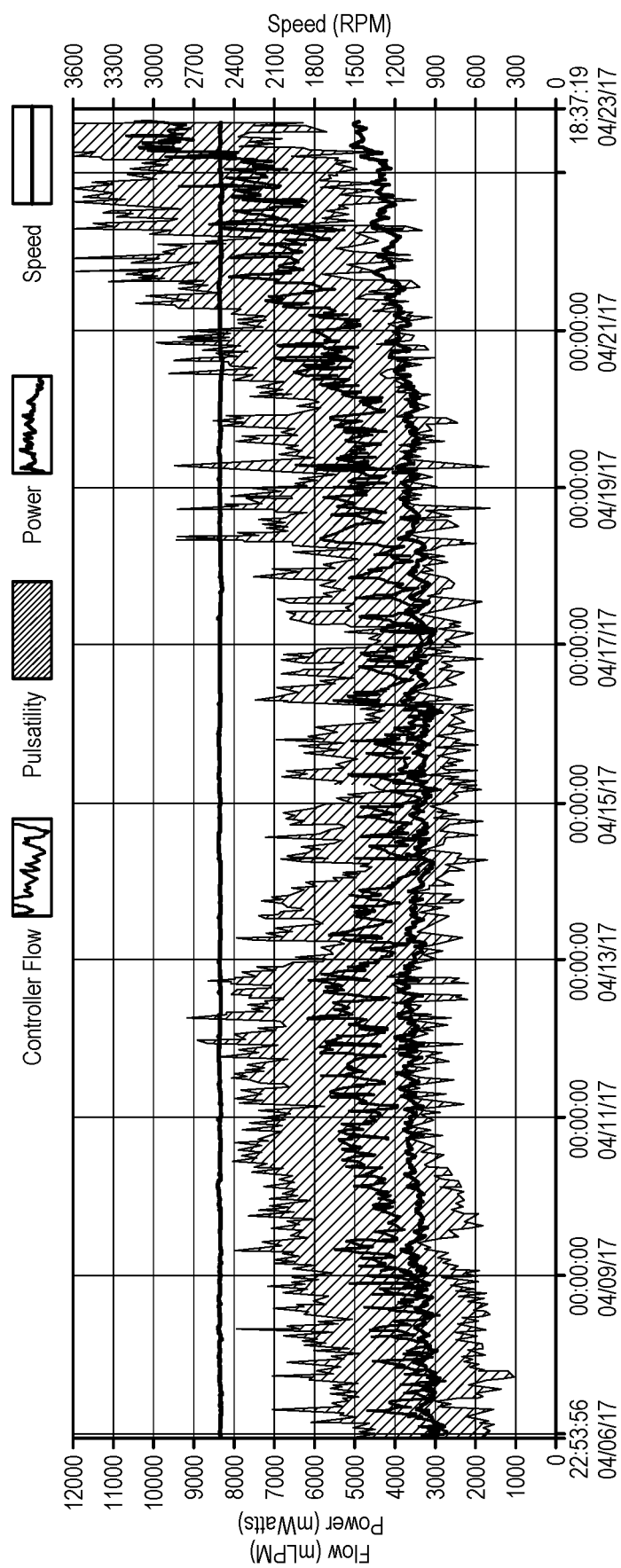
FIG. 7 is an exemplary display of a log file of an implantable blood pump operating abnormally.
Figure 8:
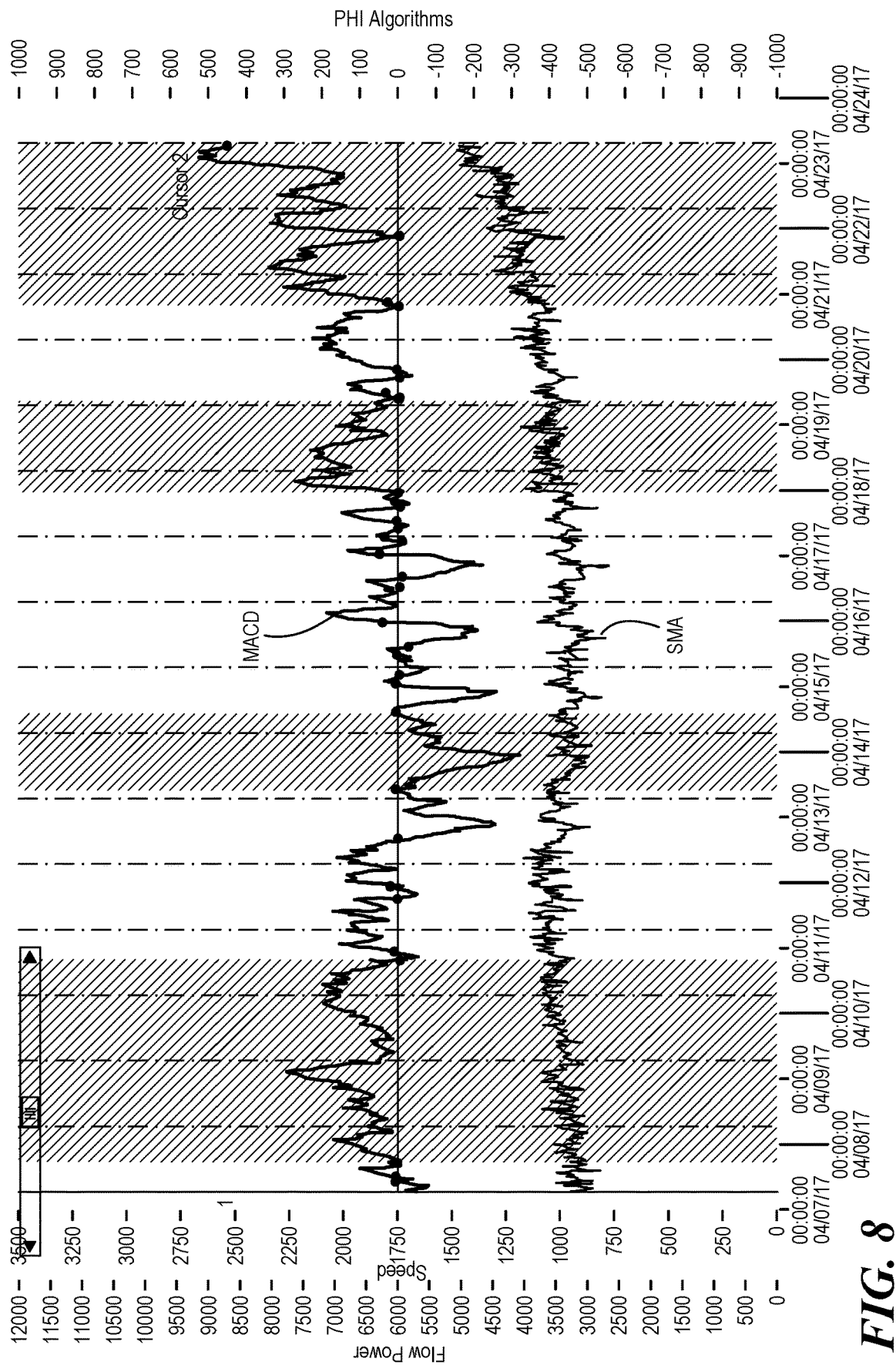
FIG. 8 is the log file of FIG. 7 with an MACD calculation displayed indicating the presence of thrombus.

Referring now to FIGS. 7 and 8, in this exemplary log file 12 of a patient whose pump is operating is not operating homeostasis, the MACD is displayed above the SMA trend line (FIG. 8). The log file indicates that between Apr. 7, 2017 and Apr. 23, 2017, there are multiple periods of time in which the MACD trend line include no zero-crossings for a period of at least 24 hour following by periods in which the MACD trend line returns to normal. The controller 10 shades the area in which no zero-crossings occur for at least 24 hours such that the physician can determine when the disruption in homeostasis of the blood pump occurred and for how long it lasted. In this particular example, the periodic lack of zero-crossings and/or the increase in the MACD trend line following about Apr. 21, 2017 is indicative of thrombus.

Figure 9:
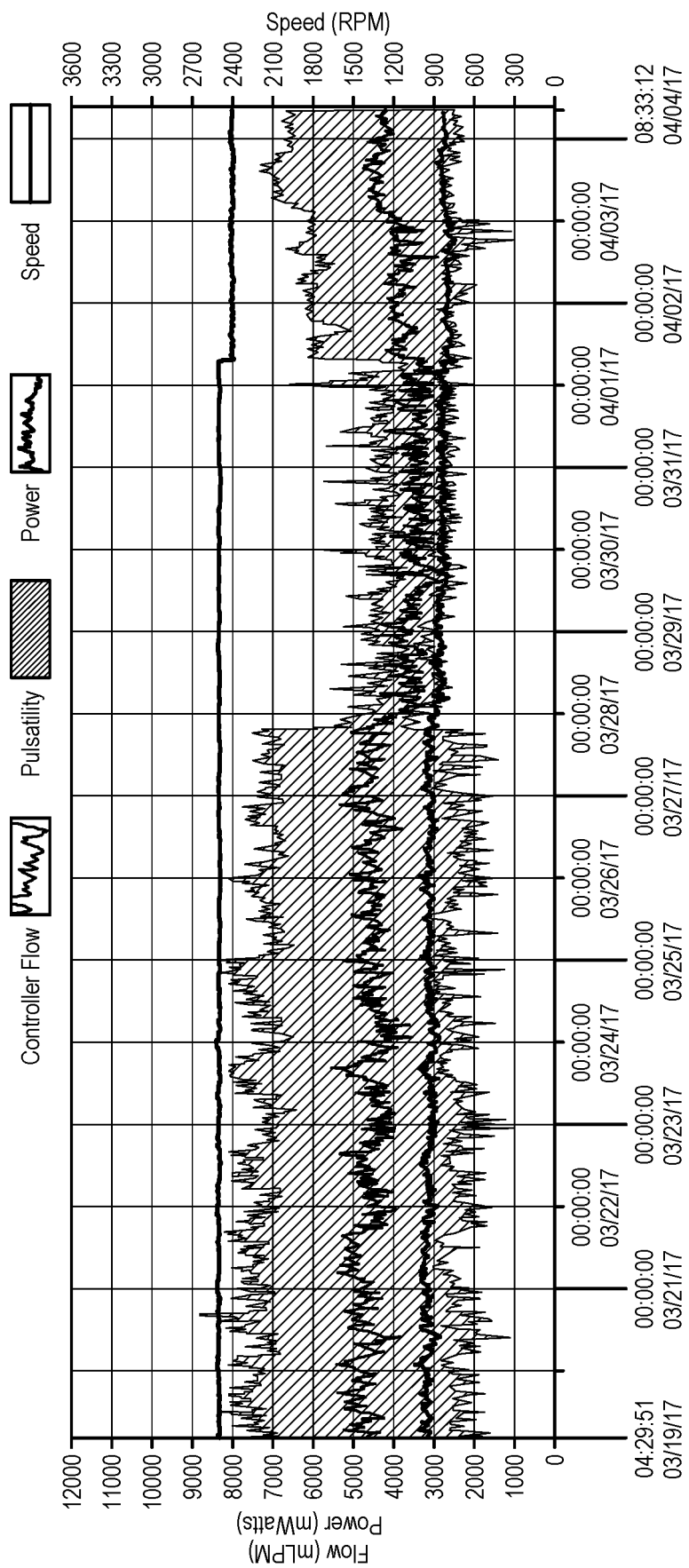
FIG. 9 is an exemplary display of a log file of an implantable blood pump operating abnormally.
Figure 10:
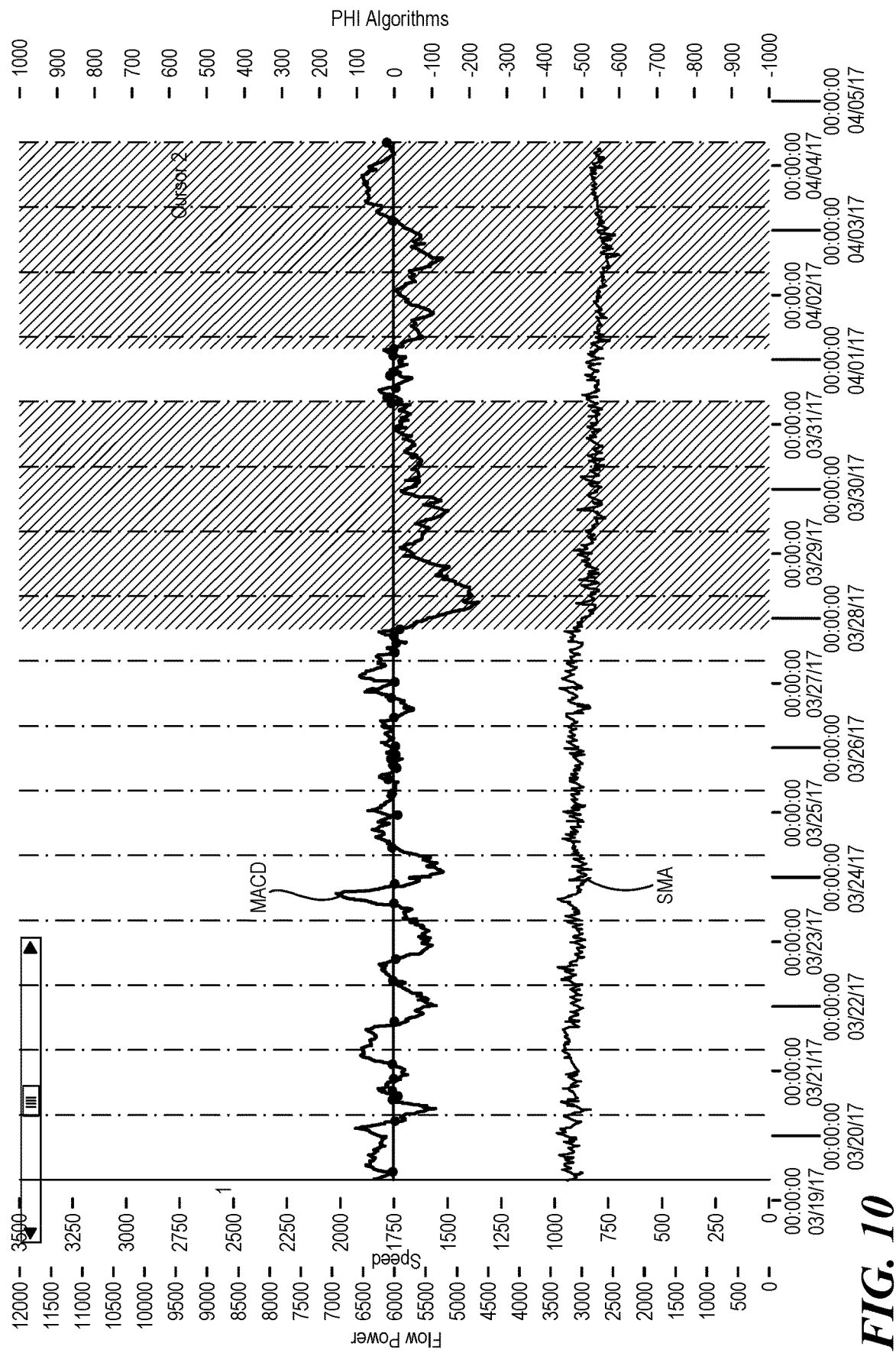
FIG. 10 is the log file of FIG. 9 with an MACD calculation displayed indicating the presence of ventricular tachycardia.

Referring now to FIGS. 9 and 10, in this exemplary log file 12 of a patient whose pump is operating is not operating homeostasis, the MACD is displayed above the SMA trend line (FIG. 10). The log file indicates that between Mar. 28, 2017 and Mar. 31, 2017 and between Apr. 1, 2017 and Apr. 4, 2017, there periods of time in which the MACD trend line include no zero-crossings for a period of at least 24 hour following by periods in which the MACD trend line returns to normal. The controller 10 shades the area in which no zero-crossings occur for at least 24 hours such that the physician can determine when the disruption in homeostasis of the blood pump occurred and for how long it lasted. In this particular example, the periodic lack of zero-crossings with a period of rapid zero-crossings is indicative of ventricular tachycardia.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of detecting a disruption in a diurnal rhythm of a patient having an implantable blood pump, comprising:
   calculating a moving average convergence divergence (MACD) based on power consumed by the implantable blood pump to maintain a constant rotational speed of an impeller of the implantable blood pump; and
   generating an alert when the calculated MACD does not cross a MACD zero line for a predetermined MACD zero line crossing time threshold.

2. The method of claim 1, wherein the MACD zero line crossing time threshold is 24 hours.

3. The method of claim 1, wherein calculating the MACD includes calculating a slow moving average (SMA), and wherein the SMA is a one second average measurement of the power consumed by the implantable blood pump measured at a predetermined interval for a first predetermined period of time.

4. The method of claim 3, wherein the predetermined interval is 15 minutes.

5. The method of claim 4, wherein the first predetermined period of time is 48 hours.

6. The method of claim 3, wherein calculating the MACD includes calculating a fast moving average (FMA), and wherein the FMA is a one second average measurement of the power consumed by the implantable blood pump measured at the predetermined interval for a second predetermined period of time less the first period of time.

7. The method of claim 6, wherein the second predetermined period of time is four hours.

8. The method of claim 1, wherein the patient has a diurnal cycle, and wherein generating the alert is indicative of a loss of the patient's diurnal cycle.

9. The method of claim 8, wherein the method further includes correlating the loss of the patient's diurnal cycle to at least one from the group consisting of thrombus and tachycardia.

10. The method of claim 1, wherein generating an alert includes at least one from group consisting of sounding an alarm on a controller of the implantable blood pump and displaying a time and date of the alert in a log file of a controller of the implantable blood pump.

11. A system of detecting a disruption in a diurnal rhythm of a patient having an implantable blood pump, comprising:
- a controller having a processor, the controller being in communication with the implantable blood pump and a power source configured to provide power to the implantable blood pump, the controller being configured to:
- calculate a moving average convergence divergence (MACD) based on power consumed by the implantable blood pump to maintain a constant rotational speed of an impeller of the implantable blood pump; and
- generate an alert when the calculated MACD does not cross a MACD zero line for a predetermined MACD zero line crossing time threshold.

12. The system of claim 11, wherein the MACD zero line crossing time threshold is 24 hours.

13. The system of claim 11, wherein calculating the MACD includes calculating a slow moving average (SMA), and wherein the SMA is a one second average measurement of the power consumed by the implantable blood pump measured at a predetermined interval for a first predetermined period of time.

14. The system of claim 13, wherein the predetermined interval is 15 minutes.

15. The system of claim 14, wherein the first predetermined period of time is 48 hours.

16. The system of claim 13, wherein calculating the MACD includes calculating a fast moving average (FMA), and wherein the FMA is a one second average measurement of the power consumed by the implantable blood pump measured at the predetermined interval for a second predetermined period of time less the first period of time.

17. The system of claim 16, wherein the second predetermined period of time is four hours.

18. The system of claim 11, generating an alert includes at least one from group consisting of sounding an alarm on a controller of the implantable blood pump and displaying a time and date of the alert on a display of a controller of the implantable blood pump.

19. The system of claim 11, wherein the controller is further configured to clear the alert when the calculated MACD crosses the MACD zero line for the predetermined MACD zero line crossing time threshold.

20. A method of detecting a disruption in a diurnal rhythm of a patient having an implantable blood pump and a diurnal cycle, comprising:
- calculating a moving average convergence divergence (MACD) based on power consumed by the implantable blood pump to maintain a constant rotational speed of an impeller of the implantable blood pump; and
- generating an alert when the calculated MACD does not cross a MACD zero line for a predetermined MACD zero line crossing time threshold, the alert being indicative of a loss of the patient's diurnal cycle, the generating an alert includes at least one from group consisting of sounding an alarm on a controller of the implantable blood pump and displaying a time and date of the alert in a log file of a controller of the implantable blood pump;
- correlating the loss of the patient's diurnal cycle to at least one from the group consisting of thrombus and tachycardia; and
- clearing the alert when the calculated MACD crosses the MACD zero line for the predetermined MACD zero line crossing time threshold.

* * * * *